United States Patent [19]

Matolcsy et al.

[11] 4,179,463
[45] Dec. 18, 1979

[54] 2-AMINO-CYCLOPENT-1-ENE-1-DITHIOCARBOXYLIC ACIDS

[75] Inventors: Gyorgy Matölcsy; Piroska Bartok, née Berencsy, both of Budapest; Bella Kiss, Vecses; Eva Palosi, Budapest; Egon Karpati, Budapest; Laszlo Szporny, Budapest, all of Hungary

[73] Assignee: Richter Gedeon Vegyeszeti Gyar Rt., Budapest, Hungary

[21] Appl. No.: 865,426

[22] Filed: Dec. 29, 1977

[30] Foreign Application Priority Data

Dec. 30, 1977 [HU] Hungary .................. RI 609

[51] Int. Cl.$^2$ ................ C07C 153/043; A61K 31/185
[52] U.S. Cl. .................. 260/502.6; 424/315
[58] Field of Search .................. 260/502.6

[56] References Cited

PUBLICATIONS

Bordas et al., "J. Org. Chem.", vol. 37 (1972), pp. 1727–1730.
Mayer et al., "J. Prakt. Chem.", 23 (1964), pp. 83–88.

*Primary Examiner*—Joseph E. Evans
*Attorney, Agent, or Firm*—Karl F. Ross

[57] ABSTRACT

2-Amino-cyclopent-1-ene-1-dithiocarboxylic acid derivatives of the formula,

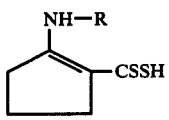

(I)

wherein R is $C_{2-4}$ alkenyl, or $C_{1-6}$ alkyl group having optionally a $C_{1-4}$ alkoxy, hydroxy, carboxy and/or amino substituent, with the proviso that if R is an unsubstituted alkyl group, this group contains at least 5 carbon atoms, are prepared by reacting 2-amino-cyclopent-1-ene-1-dithiocarboxylic acid or a salt thereof with an amine of the formula,

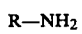

(II)

wherein R is as defined above. The new compounds of the invention exert dopamine-β-hydroxylase inhibiting effects.

6 Claims, No Drawings

2-AMINO-CYCLOPENT-1-ENE-1-DITHIOCARBOXYLIC ACIDS

This invention relates to new 2-amino-cyclopent-1-ene-1-dithiocarboxylic acid derivatives and pharmaceutical compositions containing the same, furthermore to a process for the preparation thereof.

The novel compounds according to the invention correspond to the formula,

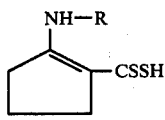     (I)

wherein R is $C_{2-4}$ alkenyl or a $C_{1-6}$ alkyl group having optionally a $C_{1-4}$ alkoxy, hydroxy, carboxy and/or amino substituent, with the proviso that if R is an unsubstituted alkyl group, this group contains at least 5 carbon atoms.

These compounds exert a dopamine-β-hydroxylase inhibiting effect.

As is known, substances influencing nervous functions exert their activities almost exclusively on the level of the stimulus transfer processes. These processes are relatively well known, thus it is possible to prepare compounds by which such processes can be influenced in a more or less controlled manner. The intervention into elementary nervous processes involves, however, not only the influencing of the nervous system itself, but also influencing the processes under the control of the nervous system. The efforts made in this respect in the last few year encompass the research work performed in connection with dopamine-β-hydroxylase and compounds inhibiting its effects.

Dopamine-β-hydroxylase catalyzes the last enzymatic step of the biosynthesis of noradrenaline, the conversion of dopamine into noradrenaline. The normal level of noradrenaline, a substance playing an essential role in the transport processes of sympathetic nervous stimuli, is an essential factor with respect to the normal nervous functions and to the normal functions of processes under the control of the nervous system. Substances with dopamine-β-hydroxylase inhibiting effects enable one to influence the noradrenergic functions. This fact is of great importance with respect of both research and therapy, since, in the field of research, the consequences of the partial or total extinction of noradrenergic functions can be examined by decreasing the noradrenaline level with dopamine-β-hydroxylase inhibitors, and, in the field of therapy, hyperfunction of the noradrenergic system can be compensated with dopamine-β-hydroxylase inhibitors. Dopamine-β-hydroxylase inhibitors can be applied in the treatment of hypertension and Parkinson's disease.

Benzyloxyamine and benzylhydrazine exert dopamine-β-hydroxylase inhibiting effects [van der Schoot et al.: Advances in Drug Research, Vol. 2, p. 47; Harper and Simmons, Nikodijevic et al.: J. Pharm. Exp. Ther. 140, 224 (1963)]. These compounds, however, exert their activities for a short period, and thus are not used in therapy. Disulfiram and diethyl dithiocarbamate, the reduction metabolite of the former compound [Goldstein et al.: Life Sci. 3, 763 (1964)], furthermore several N,N-disubstituted dithiocarbamates [Maj et al.: Eur. J. Pharmacol. 9, 183 (1970); Lippman et al.: Arch. Int. Pharmacodyn. Ther. 189, 348 (1971)] are known to exert strong dopamine-β-hydroxylase inhibiting effects. 2,2-Dipyridyl proved to be also effective under in vitro conditions [Green: Biochim. Biophys. Acta 81, 394 (1964)]. Bis(1-methyl-4-homopiperazinyl-thiocarbonyl)-disulfide in one of the most potent dopamine-β-hydroxylase inhibitors under in vivo conditions [Florvall et al.: Acta. Pharmaceut. Sulcica 7, 7 (1970)]. Aromatic and alkyl thiourea derivatives exert long-acting dopamine-β-hydroxylase inhibiting effects [Johnson et al.: J. Pharm. Exptl. Ther. 171, 80 (1970)].

Of the microbial substances fusaric acid/5-butylpicolinic acid/and its derivatives [Hidaka et al.: Molec. Pharmacol. 9, 172 (1973)], oosponol [Unmezawa et al.: J. Antibiotics 25, 239 (1972)] and dopastine [Iinuma et al.: J. Agr. Biol. Chem. 38, 2107 (1974)] are known to exert strong dopamine-β-hydroxylase inhibiting effects.

Subsequent examinations have shown that some of the known and commercially available drugs, such as hydralazine, methimazol and amphetamine, also possess dopamine-β-hydroxylase inhibiting effects.

Most of the above compounds have, however, the disadvantage that although they possess dopamine-β-hydroxylase inhibiting effects, are rather toxic in prolonged treatments, thus they can be applied in therapy in only a restricted manner, if at all.

The new compounds according to this invention possess strong dopamine-β-hydroxylase inhibiting effects and are less toxic than the known compounds with similar activities. Consequently the new compounds can be applied to great advantage in the therapy.

The dopamine-β-hydroxylase inhibiting effects of the new compounds according to the invention were examined by the following tests:

The tests were performed on male Wistar rats weighing 150 to 200 g. The dopamine-β-hydroxylase inhibiting effects of the compounds were evaluated by determining the change of noradrenaline, dopamine and adrenaline levels of the cerebrum, heart, spleen and adrenal gland. The serotonine and 5-hydroxy-indolyl-acetic acid levels of the cerebrum were also determined. The measurements were performed as follows:

The animals were decapitated, the cerebrum, heart, spleen and adrenal gland were removed quickly, and the organs were frozen by placing them onto a metal sheet cooled with dry ice. The frozen organs were stored for a maximum of one night at −20° C.

Determination of the adrenaline content of adrenal gland

The adrenal glands were freed from fat and homogenized in 3.0 ml of ice-cold 0.4 N perchloric acid. The homogenized mixtures were centrifuged for 10 minutes at 0° C. with a speed of 3200 r.p.m. on a Janetzky K-70 type centrifuge. 0.05 ml samples were taken from the supernatant, and the adrenaline level was determined directly by the method of Laverty et al. [Anal. Biochem. 22, 269 (1968)].

Determination of the noradrenaline content of heart and spleen

The organs were weighed in frozen state and then homogenized in 5.0 ml of 0.4 N perchloric acid containing 0.05% of EDTA-$Na_2$ and 0.1% of $Na_2S_2O_5$. The homogenized mixtures were centrifuged as described above for the treatment of adrenal gland, the supernatants were decanted, and the pH was adjusted to 8.0±0.1 with a 0.1 molar tris buffer containing 20 g/l of NaOH and 25 g/l of EDTA-Na$_2$. 100 mg of prepared Al$_2$O$_3$ [Anton et al.: J. Pharm. Ther. 138, 360 (1962)] were added to the samples, and the mixtures were shaken mechanically for 20 minutes. Thereafter this Al$_2$O$_3$ was washed with 2×10 ml of distilled water, and the noradrenaline was eluted with 1.0 ml of 0.05 N perchloric acid. 0.5 ml samples of the eluate were applied for the determination of noradrenaline. Noradrenaline was determined according to the method of Shellenberger et al. [Anal. Biochem. 39, 356 (1971)], with the following modifications of the basic procedure: 0.5 ml of 0.1 molar Na-K-phosphate buffer, containing 9 g/l of EDTA-Na$_2$, were added to 0.5 ml of the eluate, and the catecholamines (noradrenaline in the examination of heart and spleen and noradrenaline and dopamine in the examination of the cerebrum) were oxidized with 0.1 ml of a 0.1 N iodine solution in 5% potassium iodide. After exactly 2 minutes oxidation was stopped by adding 0.25 ml of a 2.5% sodium sulfite solution in 4.4 N aqueous sodium hydroxide to the mixture. 2 minutes after the introduction of the alkaline sulfite solution 0.2 ml of concentrated acetic acid were added to the samples, upon which the pH decreased to 4.4 to 4.5. Thereafter the samples were placed for 5 minutes into a drying oven heated to 100° C., and then the samples were cooled with ice water. The fluorescence of noradrenaline was measured with an OPTON spectrophotometer at wavelengths of 390 nm (excitation) and 490 nm (emission).

Determination of the noradrenaline, dopamine, serotonine and 5-hydroxy-indolylacetic acid contents of cerebrum The brains were homogenized in 10 parts by volume of 0.4 N perchloric acid. The homogenized mixture was stored at −20° C. overnight, thereafter it was thawed and centrifuged as described above. A sample of homogenized mixture corresponding to 0.5 g of brain was removed, the pH of the sample was adjusted to 8.0±0.1 with 0.1 molar tris-buffer of the above composition, and the sample was processed as described above for the determination of the noradrenaline content of heart and spleen, with the difference that 1.5 ml of 0.05 N perchloric acid were applied as eluting agent. 0.5 ml of the eluate were applied to determine the noradrenaline and dopamine content. The measurement was performed as described above, with the difference that samples of 0.5 ml were applied for the recording of the fluorescence of noradrenaline. The residue was placed for 50 minutes into a drying oven heated to 100° C., thereafter the sample was cooled with ice water, and the fluorescence of dopamine was recorded at wavelengths of 325 nm (excitation) and 380 nm (emission).

In a further test series the serotonine and 5-hydroxyindolylacetic acid contents were also determined, in addition to the determination of the noradrenaline and dopamine content, from the same sample. In this instance the brains were homogenized in 10 ml of 75% ethanol, 0.2 ml of EDTA-Na$_2$ and 5% of ascorbic acid were added to the homogenized mixtures, and the homogenized mixtures were maintained at −20° C. overnight. The mixtures were centrifuged as described above, and 5.0 ml samples of the supernatant were removed. The samples were diluted with equal volumes of distilled water, and poured onto ion-exchange columns of 0.5×1.5 cm dimensions, filled with buffered Amberlite CG-30 (200 to 400 mesh). The columns were washed with 5 ml of distilled water followed with 1.0 ml of 0.2 N hydrochloric acid, and the first effluent and the aqueous wash were collected for the determination of 5-hydroxyindolylacetic acid. Elution was continued with further 1.2 ml of 0.2 N hydrochloric acid in order to remove noradrenaline, dopamine and serotonine. Samples of 0.3 ml were used for the determinations.

Noradrenaline and dopamine were determined by the method of Shellenberger, modified as described above, whereas serotonine was determined by the method of Curzon et al. [Brit. J. Pharmacol. 39, 653 (1970)]. The basic method was modified as follows: A 0.5% solution of ortho-phthal-(di)aldehyde in absolute ethanol was diluted with 10 N hydrochloric acid to 50-fold of its original volume, and 0.6 ml of the resulting 0.01% ortho-phthal-(di)aldehyde solution were added immediately to 0.5 ml of the serotonine-containing sample. The sample was placed into a hot water bath for 10 minutes, thereafter cooled with tap water, and the fluorescence was recorded at wavelengths of 360 nm (excitation) and 490 nm (emission).

5-Hydroxy-indolylacetic acid was determined from the mixture of the first effluent and the aqueous wash. 10 ml of distilled water and 0.2 ml of concentrated hydrochloric acid were added to the mixture, and the sample was poured onto a 0.8×4.0 cm column filled with Sephadex G-10. The column was washed with 15 ml of 0.1 N hydrochloric acid, followed by 1.8 to 2.0 ml of 0.02 N aqueous ammonia, and then 5-hydroxyindolylacetic acid was eluted with further 2.0 ml of the aqueous ammonia. 0.5 ml samples were used in the measurements, and the determination was performed according to the method of Korf et al. [Biochem. Pharmacol. 20, 659 (1971)].

The test results are summarized in Table 1. In the tests disulfiram, 2,2-dipyridyl, bis(1-methyl-4-homopiperazinyl-thiocarbonyl)-disulfide, sodium diethyldithiocarbamate and N-phenyl-N'-(2-thiazolyl)-thiourea were used as reference substances. The values indicated in Table 1 are percentages in relation to the amine levels of the controls measured in the same test (± Standard Error). The statistical calculations were performed on a TPA/i type computer, using Student's t test.

The abbreviations used in Table 1 are as follows:
NA: noradrenaline
DA: dopamine
SE: serotonine
5-HIAA: 5-hydroxy-indolylacetic acid
AD: adrenaline
M-1: 2-(N-methoxyethyl)-amino-cyclopent-1-ene-dithiocarboxylic acid
M-2: 2-(N-allyl)-amino-cyclopent-1-ene-dithiocarboxylic acid
M-3: 2-(N-isoamyl)-amino-cyclopenta-1-ene-dithiocarboxylic acid
M-4: 2-(N-hydroxyethyl)-amino-cyclopent-1-ene-dithiocarboxylic acid
M-5: 2-[N-(4-carboxy-4-amino)-butyl]-amino-cyclopent-1-ene-dithiocarboxylic acid
M-6: 2-(N-cyclohexyl)-amino-cyclopent-1-ene-dithiocarboxylic acid
M-7: 2-[N-(5-carboxy-5-amino)-pentyl]-amino-cyclopent-1-ene-dithiocarboxylic acid
M-8: 2-(N-phenyl)-amino-cyclopent-1-ene-dithiocarboxylic acid
DS: disulfiram[bis(diethylthiocarbamoyl)-disulfide]
DDC-Na: sodium diethyldithiocarbamate
2,2-D: 2,2-dipyridyl FLA-63: bis(1-methyl-4-homopiperazinyl)-thiocarbonyl-disulfide
U-14624: N-phenyl-N'-(2-thiazolyl)-thiourea
n=number of animals

Table 1

| | | | | | Amine levels (percentages in relation to the controls) | | | | | | |
|---|---|---|---|---|---|---|---|---|---|---|---|
| | | | | | Brain | | | | Heart | Spleen | Adrenal gland |
| Comp. | Adm. | Dos. | Time | n | NA | DA | SE | 5-HIAA | NA | NA | AD |
| M-1 | i.p. | 100 | 4 | 6 | 63.4±3.6$^c$ | 106.8±4.7 | 116.0±4.7$^a$ | — | 106.1±10.3 | 77.1±8.9 | 105.6±6.1 |
| | i.p. | 200 | 4 | 12 | 64.2±3.4$^c$ | 122.0±6.7$^a$ | 106.8±2.7 | 140.6±12.3$^a$ | 110.0±7.4 | 109.5±14.1 | 91.5±4.7 |
| M-2 | i.p. | 100 | 4 | 6 | 78.6±3.3$^c$ | 107.6±2.9 | 118.3±5.7$^b$ | — | 81.3±5.1 | 74.5±10.2 | 103.4±7.6 |
| | i.p. | 200 | 4 | 6 | 71.1±3.9$^c$ | 119.3±7.0$^a$ | 109.4±5.9 | — | 122.8±11.9 | 89.9±11.0 | 71.9±4.7$^b$ |
| M-3 | i.p. | 100 | 4 | 6 | 75.2±1.7$^c$ | 103.3±4.1 | 108.4±5.7 | — | 86.9±5.9 | 48.2±9.5$^a$ | 86.2±4.5$^a$ |
| | i.p. | 200 | 4 | 6 | 68.8±2.4$^c$ | 113.6±2.7$^c$ | 98.2±3.9 | — | 131.3±4.4$^a$ | 135.1±17.0 | 73.5±2.2$^b$ |
| M-4 | i.p. | 100 | 4 | 6 | 65.4±4.9$^c$ | 109.5±3.5 | 110.0±3.3$^a$ | — | 85.0±9.7 | 81.4±9.4 | 82.7±4.2 |
| | i.p. | 200 | 4 | 5 | 41.6±2.0$^c$ | 126.5±2.5$^c$ | 122.4±10.5$^a$ | 131.8±12.6$^a$ | 75.4±8.3$^a$ | 98.4±17.1 | 93.4±7.5 |
| M-5 | i.p. | 100 | 4 | 6 | 81.7±4.5$^a$ | 100.2±4.8 | 110.0±4.1 | — | 98.4±5.4 | 76.4±11.1 | 69.4±4.0$^b$ |
| | i.p. | 200 | 4 | 5 | 69.3±2.9$^c$ | 101.6±1.8 | 113.7±3.6$^b$ | 141.4±10.0$^c$ | 75.0±10.6 | 67.1±6.2 | 70.7±3.3$^b$ |
| M-6 | i.p. | 200 | 4 | 6 | 40.7±1.1$^c$ | 107.4±5.6 | 101.2±5.1 | 149.9±8.5$^c$ | 92.7±6.5 | 98.1±13.7 | 94.9±3.4 |
| M-7 | i.p. | 200 | 4 | 6 | 65.8±3.0$^c$ | 105.9±7.2 | 99.7±6.8 | 153.4±13.0$^b$ | 95.6±8.5 | 85.3±17.7 | 79.5±6.5$^b$ |
| M-8 | i.p. | 200 | 4 | 6 | 75.6±4.6$^c$ | 97.3±7.1 | 102.0±7.9 | 134.8±10.0$^a$ | 99.9±2.9 | 71.3±12.8 | 88.4±4.6$^a$ |
| DS | i.p. | 200 | 4 | | 22.5$^c$ | 111 | 122 | — | 98 | — | 52$^c$ |
| | | 400 | 4 | | 24.1$^c$ | 112 | 117 | — | 102 | — | 66$^c$ |
| DDC-Na | i.p. | 400 | | | 64.1$^c$ | 120 | — | — | | | |
| 2,2-D | i.p. | 37.5 | 4 | | 79.5$^b$ | 116 | — | — | 104 | 100 | 80$^a$ |
| | | 75 | 4 | | 41.2$^c$ | 95 | 100 | — | 58$^b$ | — | 63$^b$ |
| FLA-63 | i.p. | 50 | 4 | | 24.6$^c$ | 118 | 124$^b$ | 134$^b$ | 96 | 58$^c$ | 43$^c$ |
| U-14624 | i.p. | 200 | 4 | | 31.6$^c$ | 121 | 137$^b$ | 175$^c$ | 106 | 111 | 72$^b$ |

Comp. = compound; Adm. = method of administration; Dos. = dosage, mg/kg; Time = period of treatment, hours
$^a$0.01 < p < 0.05
$^b$0.001 < p < 0.01
$^c$p < 0.001

The data of Table 1 clearly demonstrate that the new compounds according to the invention considerably decrease the noradrenaline level in the brain. Depending on the dosage, the method of administration and the duration of treatment, the extent of decrease is 50 to 70%. At the same time a considerable (20 to 30%) increase in dopamine level can also be observed. The increase of serotonine level is less significant, the 5-hydroxy-indolylacetic acid level increases, however, occasionally by 50 to 90%.

The noradrenaline levels of heart and spleen, and the adrenaline levels of the adrenal gland decrease as well, these decreases are, however, not always significant even for compounds strongly decreasing the cerebral noradrenaline level. This phenomenon can be attributed presumably, to the fact that the catecholamine turnovers of these organs are slow, furthermore that adrenal gland possesses a relatively great depot of catecholamines (noradrenaline and adrenaline), and the missing noradrenaline contents of the spleen and heart are quickly supplemented by circulation. A unequivocal decrease of catacholamine levels cannot be observed in these organs with the known dopamine-β-hydroxylase inhibitors, either.

The toxicity data of the compounds according to the invention are as follows:

Table 2

| Compound | Animal | Method of administration | LD$_{50}$ mg/kg |
|---|---|---|---|
| M-1 | mice | i.p. | ~400 |
| M-2 | mice | i.p. | ~500 |
| M-4 | mice | i.p. | ~800 |
| M-5 | mice | i.p. | ~700 |
| M-6 | mice | i.p. | >1000 |
| M-7 | mice | i.p. | ~900 |
| M-8 | mice | i.p. | >1000 |
| FLA-63 | mice | i.p. | ~150 |
| 2,2-D | mice | i.p. | 280 |

Table 2-continued

| Compound | Animal | Method of administration | LD$_{50}$ mg/kg |
|---|---|---|---|
| | rats | i.p. | 150 |
| Hydralazine | mice | i.p. | 83 |
| DS | rats | p.o. | 8600 ± 370 |
| | rabbits | p.o. | 1800 ± 130 |
| Dopastine | mice | i.p. | 250 – 500 |
| | | i.p. | 460 |
| | | p.o. | 750 |
| Fusaric acid | mice | p.o. | 230 ± 25 |
| Chlorofusaric acid | mice | p.o. | 470 ± 85 |
| Oosponol | mice | i.p. | 40 |
| | | p.o. | 280 |
| U-14624 | mice | i.p. | ~680 |
| | | p.o. | >1000 |

The data of Table 2 indicate that the LD$_{50}$ values of the new compounds according to the invention are very favourable, thus these compounds can be administered for a prolonged time.

The new compounds of the general formula (I) are prepared according to the invention by reacting 2-amino-cyclopent-1-ene-dithiocarboxylic acid or a salt thereof with an amine of the general formula (II)

$$R-NH_2 \qquad (II)$$

wherein R is as defined above. The reaction is performed in a manner known per se [Bordás et al.: J. Org. Chem. 37, 1727 (1972)]. 2-Amino-cyclopent-1-ene-dithiocarboxylic acid and the amines of the formula (II), used as starting substances, are known compounds.

The reaction is performed, preferably, in a solvent medium, such as in an inert organic solvent (e.g. analcohol) or in an aqueous inert organic solvent. The reaction is carried out preferably at elevated temperatures, particularly at the boiling point of the reaction mixture.

The invention is described in detail by the aid of the following non-limiting Examples.

EXAMPLE 1

2-(N-Allyl)-amino-cyclopent-1-ene-1-dithiocarboxylic acid 6.0 g (0.2 moles) of allylamine are added to a suspension of 7.1 g (0.04 moles) of ammonium 2-amino-1-cyclopent-1-ene-1-dithiocarboxylate in 60 ml of methanol, and the mixture is refluxed for 3 hours. The mixture is cooled, diluted with 180 ml of water, decolourized with charcoal, and filtered. The filtrate is acidified with 12 ml of acetic acid. The separated substance is filtered off, washed with water and dried in a vacuum desiccator. The title compound, melting at 100°–104° C., is obtained with a yield of 48%.

Analysis: Calculated: S: 32.3%, N: 7.03%; Found: S: 31.5%, N: 6.7%.

EXAMPLE 2

2-(N-Isoamyl)-amino-cyclopent-1-ene-1-dithiocarboxylic acid or
2-{N-[(2,2-dimethyl)propyl]}-amine-cyclopent-1-ene-1-dithiocarboxylic acid 17.0 g (0.2 moles) of isoamylamine are added to a solution of 12.6 g (0.08 moles) of 2-amino-cyclopent-1-ene-1-dithiocarboxylic acid in 120 ml of methanol. The mixture is refluxed for 3 hours, then it is cooled, diluted with 360 ml of water, and filtered. The filtrate is acidified with 12 ml of acetic acid. The separated solid is filtered off, washed with water, and taken up in a mixture of 30 ml of water and 20 ml of 10% sodium hydroxide solution. The non-dissolved substance is removed by filtration, and the filtrate is acidified with acetic acid. The separated substance is filtered off, washed with water, and dried in a desiccator. The named compound, melting at 65°–79° C., is obtained with a yield of 3.62%.

Analysis: Calculated: S: 27.9%, N: 6.1%; Found: S: 27.5%, N: 6.17%.

EXAMPLE 3

2-[N-(4-Carboxy-4-amine)-butyl]-amino-cyclopent-1-ene-1-dithiocarboxylic acid

A suspension of 3.36 g (0.02 moles) of 2-ornithine hydrochloride and 5.0 g (0.06 moles) of sodium hydrocarbonate in 50 ml of methanol and 15 ml of water is refluxed for 1.5 hours. Thereafter 20 ml of methanol and 3.52 g (0.02 moles) of 2-amino-cyclopent-1-ene-1-dithiocarboxylic acid ammonium salt are added to the mixture, and refluxing is continued for further 10 hours. The mixture is cooled, diluted with 200 ml of water, decolorized with charcoal, and filtered. The filtrate is acidified with 25 ml of acetic acid. The separated substance is filtered off, washed with water and dried in a desiccator. The named compound, melting at 155° C., is obtained with a yield of 15.5%.

Analysis: Calculated: S: 23.4%, N: 10.2%; Found: S: 26.04%, N: 7.86%.

EXAMPLE 4

2-(N-Methoxyethyl)-amino-cyclopent-1-ene-1-dithiocarboxylic acid 15.0 g (0.2 moles) of 2-methoxyethylamine are added to a suspension of 12.6 g (0.08 moles) of ammonium 2-amino-cyclopent-ene-1-dithiocarboxylate in 120 ml of methanol. The mixture is refluxed for 3 hours, then it is cooled, diluted with 360 ml of water, and the hazy mixture is decolourized with charcoal. 12 ml (0.2 moles) of acetic acid are added to the resulting light red solution. The separated yellow, amorphous substance is filtered off, washed with water, and dried in a vacuum desiccator. 6.1 g of the resulting crude product are taken up in 50 ml of water, 20 ml of 10% sodium hydroxide solution are added, and the mixture is stirred for some minutes. The insolubles are filtered off on a rumpled filter and washed with a small amount of water. The clear filtrate is admixed with acetic acid to precipitate the product completely. The precipitate is filtered off, washed with water, and dried in a desiccator. The named compound, melting at 64°–70° C., is obtained with a yield of 35.7%.

Analysis: Calculated: S: 29.4%, N: 6.45%; Found: S: 29.4%, N: 5.81%.

What we claim is:

1. A 2-(substituted amino)-cyclopent-1-ene-1-dithiocarboxylic acid of the formula I

wherein R is, $C_{1-6}$ alkyl having a $C_{1-4}$ alkoxy, hydroxy, and both a carboxy and an amino substituent.

2. 2-(N-Methoxyethyl)-amino-cyclopent-1-ene-dithiocarboxylic acid.

3. 2-(N-Hydroxyethyl)-amino-cyclopent-1-ene-1-dithiocarboxylic acid.

4. 2-[N-(4-Carboxy-4-amino)-butyl]-amino-cyclopent-1-ene-1-dithiocarboxylic acid.

5. 2-[N-(5-Carboxy-5-amino)-pentyl]-amino-cyclopent-1-ene-1-dithiocarboxylic acid.

6. A compound according to claim 1 selected from the group consisting of
2-(N-methoxyethyl)-amino-cyclopent-1-ene-dithiocarboxylic acid;
2-(N-hydroxyethyl)-amino-cyclopent-1-ene-1-dithiocarboxylic acid;
2-[N-(4-carboxy-4-amino)-butyl]-amino-cyclopent-1-ene-1-dithiocarboxylic acid;
2-[N-(5-carboxy-5-amino)-pentyl]-amino-cyclopent-1-ene-1-dithiocarboxylic acid.

* * * * *